FRACTION CAPABLE OF INDUCING IN VIVO A RESISTANCE TO BACTERIAL INFECTIONS, PROCESS FOR OBTAINING SAID FRACTION FROM BACTERIA AND DRUGS CONTAINING SAID FRACTION

The invention relates to a fraction capable of inducing in vivo a resistance to bacterial infections, to a process for obtaining said fraction from bacteria, particularly gram negative bacteria. It also relates to drugs containing said fractions as active principles. Since TEAGUE and MCWILLIAMS who published results of their first work in 1917, much has been written on the properties of gram negative bacteria, more particularly the very their lipopolysaccharides (LPS), also known under the name of endotoxines, which have been held responsible up to day of the various properties which will be referred to hereafter.

From the literature on the subject it appears that these lipopolysaccharides (LPS) have the valuable property of inducing a resistance in vivo to bacterial infections. Some of these LPS are also deemed capable of favouring tumor necrosis and/or to also possess immunostimulant, adjuvant or mitogenic properties. Unfortunately, these LPS also exhibit important toxical effects (lethality, shocks, pyrogenicity), so that it has not been seriously contemplated to take advantage of the very valuable properties which the LPS possess in human or veterinary therapy.

This toxicity is such that, for instance, a dose of 0.1 microgram (mcg) of endotoxine prepared starting from *Salmonella enteritidis* causes death of 5 mice out of 5 to which it is administered intravenously, when these mice have previously been sensitized to endotoxines by 12.5 mcg of actinomycine D, administered intraperitonaleously. This toxical dose of endotoxine which causes death in mice within a 24 hours' period falls down to 5 nanograms (ng), when administered to surrenalectomized mice. As a matter of fact surrenalectomization induces a considerable sensitivity of the so-treated mice to endotoxines.

Many authors have tried to modify the LPS under the action of physical, chemical or biological agents, to suppress the toxical properties without substantially modifying their valuable properties, particularly their capability of inducing a resistance to bacterial infection, which effect could be taken advantage of with great benefit in therapy.

The knowledge which one presently has of the different components of bacterial walls, particularly of their LPS, as well as of their other components, such as those which are comprised between the exterior membranes and the rigid layer which also contains the mureine (also known as "mucopeptide" or "peptidoglycan") of the bacterial wall, is, among others, to be ascribed to the different attempts which have been made for the above mentioned purpose. However, very little has been achieved in connection therewith, at least to such a sufficient degree to make them useful in therapy.

Among the numerous attempts which have been made, one may cite those which consisted of subjecting the toxical fractions to the action of enzymes. For instance, TAUBER and RUSSEL (Exptl. Med. Surg. 19, 161 (1961) have studied the action of a series of enzymes, such as lysozyme, cristallized trypsine, chymotrypsine, pancreatic lipase and lipoproteinlipase, on endotoxines obtained starting from different species of *Neisseria, Escherichia* and *S. abortus equi*, under substantially neutral pH conditions. The authors reached the conclusion that the endotoxins so treated had neither been hydrolysed nor detoxified.

Many other authors have described detoxification attempts of various endotoxins with various enzymes thereby obtaining results which can be considered as insufficient, or absent. Somewhat better results were obtained by KIM and WATSON (Proc. Soc. Exptl. Biol. Med. 115, 140 (1964)) with an activated papain on endotoxins obtained from *E. coli* 08 (C008) and *S. enteritidis* (SE) in an acidified medium, at pH 4. These authors asserted the hypothesis that the detoxification might be due to an effective hydrolysis of the treated endotoxins by the activated papain. This hypothesis has however been challenged by other authors, notably RUDBACH et al. (Proc. Soc. Exptl. Biol. Med. 119, 115 (1965)) who studied the results of KIM and WATSON and asserted on the contrary, the reduction of toxicity and more particularly of pyrogenicity which had been observed might be ascribed to the formation of a complex between the endotoxin and the papain rather than to the hydrolysing action of the latter.

Generally speaking, it has thus been found that under the operating conditions which have been recalled hereabove, the reduction of the toxicity obtained has not been significant, in any case not sufficient for permitting the use of the so-treated extracts to be considered in therapy, more particularly for the effective induction of a protection against bacterial infections.

In the course of the research work which has been referred to hereabove, it had already been proposed to separate those of the fractions which could be solubilized in an aqueous phase or solution from the insoluble fractions which were obtained, respectively, as a result of the above mentioned hydrolytic or enzymatic treatments of the starting lipopolysaccharide. The endotoxic properties of either one or the other of the fractions so separated were then assessed and, if appropriate, compared to the endotoxic properties of the starting endotoxic extract. It is however significant to recall that the authors under consideration did not think of isolating more particularly from the above said hydrosoluble fractions, various hydrosoluble sub-fractions respectively formed of components, the molecular weights of which are comprised within determined ranges for the sake of checking in each of said sub-fractions whether the toxicity, on the one hand, and other biological properties, more particularly their capability to induce a protection against bacterial infection, on the other hand, had been preserved.

Among the few authors who attempted that approach, OROSZLAN and MORA (Biochem. Biophys. Res. Commun. 12, 345 (1963)) and RIBI et al. (J. Bacteriol. (1966), 92, 143) suggested to resort to detergents and surfactants in order to achieve the dissociation of the macromolecular complexes which the LPS form, into sub-units of lower molecular weights. They however found that the sub-units obtained under the experimental conditions disclosed had lost most of their desirable biological activity and, moreover, that they reaggregated into particles having a higher molecular weight as soon as the detergent or surfactant was removed.

Particularly, RIBI et al state that endotoxins obtained from *E. coli*, by a phenol extraction treatment could be dissociated to obtain sub-units having an average molecular weight of approximately 20,000 in presence of

United States Patent [19]

Choay et al.

[11] 4,148,877

[45] Apr. 10, 1979

[54] FRACTION CAPABLE OF INDUCING IN VIVO A RESISTANCE TO BACTERIAL INFECTIONS, PROCESS FOR OBTAINING SAID FRACTION FROM BACTERIA AND DRUGS CONTAINING SAID FRACTION

[75] Inventors: Jean Choay, Paris; Mireille Sakouhi nee Cousin, Gif-sur-Yvette, both of France

[73] Assignee: Choay S. A., Paris, France

[21] Appl. No.: 752,993

[22] Filed: Dec. 21, 1976

[30] Foreign Application Priority Data

Dec. 29, 1975 [FR] France ............................. 75 40041
May 19, 1976 [FR] France ............................. 76 15093

[51] Int. Cl.$^2$ ..................... A61K 39/02; C12D 13/10
[52] U.S. Cl. ............................................. 424/92; 195/4
[58] Field of Search ................... 424/87, 92, 95; 195/4

[56] References Cited

U.S. PATENT DOCUMENTS

| | | | |
|---|---|---|---|
| 1,621,118 | 3/1927 | Larson | 424/87 |
| 2,020,647 | 11/1935 | Hunwicke | 424/92 |
| 3,132,995 | 5/1964 | Berger | 424/92 |
| 3,600,378 | 8/1971 | Marsh et al. | 424/92 |
| 4,013,788 | 3/1977 | Jolles et al. | 424/92 |
| 4,029,762 | 6/1977 | Galanos | 424/92 |

FOREIGN PATENT DOCUMENTS

| | | | |
|---|---|---|---|
| 817394 | 7/1969 | Canada | 424/92 |
| 2134930 | 1/1972 | Fed. Rep. of Germany | 424/92 |
| 2035795 | 12/1970 | France | 424/92 |
| 535089 | 3/1941 | United Kingdom | 424/87 |

Primary Examiner—Donald B. Moyer
Attorney, Agent, or Firm—Weiser, Stapler & Spivak

[57] ABSTRACT

A biologically active fraction of reduced toxicity or substantially free of it formed of components having molecular weights not exceeding 10,000–12,000, capable of stimulating in vivo the resistance to bacterial infections, is obtained from bacteria, more particularly Gram-negative bacteria.

A process to that effect consists of subjecting a solution of an hydrosoluble crude bacterial extract to the action of an enzyme, such as DNase, which is capable of causing the irreversible detachment of the above said biologically active fraction from the hydrosoluble crude extract which can then be separated, such as by a filtration procedure, from the other components of the hydrosoluble crude extract. The latter can be obtained such as by the treatment of bacteria with a water-phenol mixture, preferably at a temperature above ambient, from about 60° to about 70° C., or by the action on bacteria of a detergent such as sodium dodecyl sulfate.

The biologically active fraction according to the invention is useful for stimulating the immunological defense and for preventing or treating bacterial infections in a host.

12 Claims, No Drawings tion, evaporation of the solvet or lyophilization of the solution, if need be after first concentration thereof.

It must be understood that the hydrosolubility of the extract termed hereabove "hydrosoluble crude extract" means essentially that the "crude extract" is contained in the aqueous phase obtained as the result of any process for producing it starting from bacteria, particularly gram negative bacteria, after the removal of the solid or insoluble residues obtained as a result of the extraction procedure and, if appropriate, of another non aqueous or water immiscible phase.

As a general rule, the hydrosoluble "crude extract" which forms the starting material to be contacted later with the enzymatic agent is obtained as a result of the solubilization of part, if not all, of the components of the exterior layers of the bacterial walls which may be solutilized in water. In addition, this "crude hydrosoluble extract" is expected to also contain substances which participate to the biosynthesis of LPS and of endocellular components. This ∓hydrosoluble crude extract" can still exhibit a considerable toxicity.

Generally speaking this "crude extract" can be obtained by any method which authorizes the extraction with an aqueous solution of the components solubilizable in water of the treated bacteria, the essential condition at this stage being that the capability of inducing a resistance to bacterial infections of the type known for LPS be preserved in the solubilized fractions.

The invention thus is derived from the discovery that fractions of low molecular weights, which exhibit said capability of inducing a resistance to bacterial infections while being substantially devoid of toxicity, can be separated from said hydrosoluble "crude extract". This separation must however be carried out under mild conditions, taking into account the fact that said fractions of low molecular weight can be inactivated at acid pH values, particularly at a pH lower than 6 or at alkaline pH values, notably higher than 9.5.

An advantageous source for the above said "crude extract" as defined above, is formed of the gram negative bacteria of the Enterobacteriaceae genus. It can be noted that the LPS of the bacteria of this genus have in common a lipid A which is subject only to extremely minor variations. Among the enterobacteriaceae, the Salmonellae form a preferred class of bacteria from which "biologically active fractions" substantially devoid of toxicity can be obtained.

The hydrosoluble "crude extract" which forms the starting material to which the process according to the invention is applied, is for instance formed of the aqueous phase which can be obtained by subjecting gram negative bacteria to the well-known process of Westphal for separating their endotoxins. It will be recalled that this process comprises subjecting gram negative bacteria or their cell walls to the action of a phenol-water mixture at a temperature of 60°-70° C., the respective amounts of phenol and of water being such that the final proportions in volume of phenol and of water in the reaction medium be substantially equal. The hydrosoluble "crude extract" is then contained in the aqueous phase which, after separation of the phenolic phase, can be lyophilized, if need be after a prior concentration. It may be noted at this stage that an attempt to separate by physical means active fractions formed of components having molecular weights lower than 10,000 from the above mentioned aqueous phase or a solution obtained by redissolving the above said lyophilisate in an aqueous solution, shall not provide a "biologically active fraction" meeting the criteria which have been defined hereabove. The same applies when the aqueous phase or the aqueous solution are first recontacted with phenol at an elevated temperature.

A preferred "crude extract" is however formed of that which is obtained by treating gram negative bacteria with a detergent within an aqueous solution. This procedure enables generally a greater yield in "active crude extract" than the classical Westphal method (for instance 10% of dry product, when the treated bacteria are formed of Salmonella enteritidis and/or the detergent is sodium dodecyl sulphate (SDS) instead of 2.5%. It is then also possible to obtain greater amounts of the "biologically active fraction" according to the invention.

In a general manner the bacteria or their walls are contacted with the detergent within an aqueous medium. Preferably recourse is had to a detergent which has a strength such and which is used in a medium such that, under the conditions of treatment, particularly of temperature and duration, at least the exterior part of the treated bacteria which comprises the LPS and preferably also the layers immediately underneath the exterior layers be solubilized. The detergent may also provoke a rupture of the external layers of the bacteria, whereby greater amounts of the substance can be freed in the medium. Particularly, active substances could also be provided by the interior layers of the cell walls and by the cytoplasm.

The "crude extract" is then formed of the contents of the aqueous phase obtained, after separation of the non solubilized bacterial material and removal of the detergent.

In a preferred embodiment of the process according to the invention, the bacteria or bacteria walls are first partially delipidated by treatment with any of the usable delipidation organic solvents, prior to being subjected to the action of the detergent. Among the usable delipidation solvents, one may cite chloroform, methanol, aceton, ether, isoamylic alcohol, etc, these solvents being used singly or in admixture, or one after the other in conventional sequential delipidation treatment.

The many detergents which can be used are well known from the man skilled in the art. In addition to the LPS already mentioned, recourse can be had for instance to the mono p-(tetramethyl-1,1,3,3-butyl) phenylether or polyethylen-glycol also known under the commercial designation "TRITON X 100" or the petroleum or kerosene extract commercialized by the SHELL Company under the commercial designation "NONIDET P40", etc.

The treatment of the bacteria with the detergent is preferably carried out within an aqueous solution at a pH of 6.5-8.5, particularly in a buffered solution of a substantially neutral pH, such as a Tris $10^{-2}$M aqueous solution (based on tris-hydroxy-methyl-aminomethan) having a concentration ranging for instance from about 0.1 to 10%, preferably from 0.4 to 5%, such as of the order of 4%, of the detergent for a duration which can range from 5 minutes to 1 hour and at a temperature ranging from ambient to reflux, preferably between 50° and 100° C., often at reflux.

The preceding indications have but an examplary value for the different parameters which are available to the man skilled in the art, for carrying out a choice, if need be after a few experimental vertifications, of the most favourable conditions for obtaining from a chosen bacterial strain the "crude extract" which will from the starting material from which the "biologically active fractions" according to the invention, having reduced toxicity or being devoid of it, can be "detached." In a general manner, the detergent and the conditions of the treatment will be selected in a manner such that, at least part of, if not all of the valuable activity of the bacteria be contained in the crude extract. The presence of this activity in the extracted portions of the bacteria can be checked for instance by means of the test which consists of verifying the existence in mice of the protecting effffect against bacterial infections of the "crude extract" obtained in doses however lower than their lethal dose in the animal subjected to the test.

The removal of the detergent from the aqueous phase obtained can be achieved in any manner known per se. Advantageously, recourse is had to a precipitation of the active fractions obtained in the aqueous phase or solution under conditions such that the detergent remains within the solution. This precipitation from the solution can be carried out with usual organic solvents such as alcohol, at ambient temperature or at a temperature lower than ambient, for instance at 6° C. Preferably the precipitate is then taken up into an aqueous solution, notably a buffered solution, the latter being then subjected to dialysis for eliminating the ions and the possible remaining traces of the SDS. The dialysate can then be lyophilised, if need be after a first concentration of the solution, whereby a crude extract is obtained which can be subjected to the process according to the invention for causing the removal of the "biologically active fractions," according to procedures, among which the preferred ones which will be indicated hereafter.

At this stage the "crude extract" obtained is generally highly active, however also very toxic. At this stage the "crude extract" may still undergo further purification procedure in order to provide fractions having an even greater speecific activity.

In that respect the hydrosoluble "crude extract" may be subjected to a deproteinization treatment. Although proteins which may still be present in the medium either in free state or bound to other components of the medium, do not seem to take part in the separation procedure of the "biologically active fraction" substantially devoid of toxicity, their presence may merely result in a reduction of the specific activity of the "biologically active fraction" finally obtained. The said proteins may also disturb to some extent the action of the enzymes used in the detachment procedure of the "biologically active fraction."

While this deproteinization is achieved at least in part on those "crude extracts" which have been obtained by the classical Westphal extraction procedure of endotoxins already mentioned above, this is not the case generally for the hydrosoluble "crude extracts" which have been obtained by the action of a detergent on the bacteria or bacteria cell walls. In the latter case, the deproteinization may then be achieved by applying to the "crude extract" itself, the phenol-water technique conventionally used for separating the endotoxines from bacteria. As already indicated the phenol-water extract is not liable of causing the separation of the non toxic "biologically active fraction" according to the invention from the "crude extract", even at temperatures above ambient.

A preferred process for removing proteins of the "crude extract" then consists of subjecting an aqueous solution thereof, preferably buffered at neutral pH, with phenol, if need be at a temperature above ambient. The aqueous phase which then results from the aqueous medium separated from the phenolic phase, and the washings thereof can then further be subjected to purification procedures aiming at removing the mineral salts of the buffer, such as by dialysis and the residual traces of phenol, such as by diafiltration. The deproteinized "crude extract" can be obtained starting from the aqueous solution in a manner known per se, for instance by alcoholic precipitation. In this last case resource is advantageously had to a redissolution of the precipitate obtained in an aqueous buffer at neutral pH, the solution obtained being then lyophilized the lyophilizate or an aqueous solution of this lyophilizate then forms the preferred "crude extract" which is then subjected to the separation procedure for obtaining the "biologically active fraction" according to the invention.

This separation procedure can then be carried out under the conditions disclosed hereafter, either directly on the aqueous solution, or after a preheating treatment of the aqueous solution.

As a matter of fact and according to the preferred additional feature of the process according to the invention, the solution of the hydrosoluble "crude extract" is subjected to a preheating treatment at a temperature which may be up to 100° C., at substantially neutral pH. As a matter of fact it has been found that such preheating tends to render more sensitive or fragile what appears to be the bond of the desired components of low molecular weight to the components having a higher molecular weight, notably higher than 10,000, which are contained in the hydrosoluble "crude extract". The eventual separation of the components of low molecular weight will then become easier.

The enzymes which may be used for carrying out the separation of the "biologically active fraction" according to the invention from the components contained in the "crude extract" can be any of those which will enable the separation of components of molecular weights lower than or at most equal to 10,000–12,000 and in which the biological properties, more particularly the capability to induce a protection against bacterial infection will be preserved. The preservation of this property can in fact be found in the fractions of lower molecular weight which may have detached from the "crude extract" in the course of the enzymatic treatment, only after the separation of the enzyme and of the remaining components having higher molecular weight. One test which can be used for recognizing those of the enzymes which can be used may again be based on the determination of whether the fractions of low molecular weight obtained are still capable of protecting mice against the above mentioned Klebsiella, without at the same time inducing endotoxic shock and lethality in mice which have previously been sensitized to endotoxines by the actinomycine D and this at doses up to 10 micrograms per animal.

Among the enzymes which are capable of causing the above said detachment or separation, one may cite at first the nucleases, particularly the desoxyribonucleases (DNAses), certain lipases, such as pancreatic lipase or the lipase which can be extracted from Rhizopus or from *Candida alibcans*. A preferred lipase is that extracted from Rhizopus. Other enzymes such as phosphatases, phosphodiesterases and proteases can be resorted to also.

Obviously, treatment can be repeated with distinct enzymes used in different sequences or with a mixture of enzymes.

The enzymatic treatment will normally be carried out within an aqueous solution, preferably at the pH at which the enzyme used will have optimal effectiveness, such as at pH comprised between 7 and 8, say at pH 7.6.

The recovery of the "biologically active fraction" of low molecular weight separated from the toxic fractions having higher molecular weights can be achieved in any known manner per se. Advantageously recourse will be had to filtrations on ultrafiltration membranes such that they will allow for the passing therethrough only of molecules which have a molecular weight not higher than the maximum value chosen, that is approximately 10,000. Use can also be made of molecular sieves, it being then understood that only those portions of the eluate which contain components the molecular weights of which are at most equal to approximately 10,000 are then recovered.

The biologically active components according to the invention which are at the same time substantially free of toxicity and which are contained in the ultrafiltrates obtained can then be recovered such as by lyophilization.

After treatment the enzyme may be deactivated in any manner known per se. It can be separated at the same time as the components having higher molecular weights, particularly if its own molecular weight is substantially higher than 10,000, when the above said separation is carried out by filtration. This is particularly so when the enzyme used is a DNase having a molecular weight of the order of 30,000.

It has often been found that in such situations additional proportions of "biologically active fractions" of reduced toxicity or even substantially devoid of toxicity can be further detached or separated from the components of higher molecular weight which are retained on the filter, by reincubating a solution thereof with the enzyme. The new amounts of "biologically active fractions" can then be recovered in the same manner as recalled hereabove.

The fractions so obtained are highly active. Particularly, it has been found that doses of one microgram and even less of an active fraction so obtained is usually able, when administered to mice intravenously, to protect 10 animals out of 10 which are injected one day later with $1.5 \times 10^6$ cells of Klebsiella (*Klebsiella pneumoniae* strain ATCC N° 9997). As such the active fractions so obtained are part of the invention.

It has however been found that in some instances the fractions so obtained still exhibit some pyrogenicity owing to the presence in said fractions of some pyrogenic substances which in fact may originate from the ultrafiltration membranes, when of a polysaccharidic nature, and which may be entrained in the filtrate during the ultrafiltration or diafiltration procedure.

According to an additional preferred feature of the invention, advantage is then taken of the above said thermal stability of the biologically active fractions of the invention for destroying or inactivating the pyrogenic substances possibly still present in said fractions by a post-heating treatment.

More specifically the additional process step of the invention will then consist of subjecting a solution of said biologically active fraction to a temperature above 103° C., yet not exceeding that which would cause said biologically active fraction to lose its desirable properties, that is above 180° C. Preferably the temperature of the heat treatment will then be comprised between 104° C. and 107° C. for a time sufficient to cause inactivation of the pryogenic substances. This treatment may involve some reduction of the biological activity, this loss being perhaps due either to a partial degradation of part of the components contained in the "biologically active fraction" or to the degradation of a toxic contaminant. In any case fractions will be obtained which, at a dose lower than 20 micrograms, will be capable of inducing protection of mice according to the standard test referred to hereabove.

A further disclosure of preferred process embodiments will be described hereafter for the sole sake of further illustrating the invention, yet without limiting it, said preferred process embodiments being applied to gram negative bacteria, particularly to Entero-bacteriaceae, such as *Salmonella enteritidis*.

(1) Delipidation of the bacteria

Starting from the washed bacteria isolated from a bacteria strain obtained in a manner known per se, bacterial cells are delipidated so as to separate and eliminate, at least partially, the slightly bound external lipids by means of a treatment in polar organic solvents, more especially a chloroform/methanol mixture containing at least 10 volumes and preferably 24 volumes of chloroform for 1 volume of methanol, during at least 12 hours, probably 24 hours, under stirring. The cells are then separated by centrifugation and solvent traces are eliminated by means of several washings, preferably 5 successive washings, with a buffer having a pH of about 8, preferably a Tris $10^2$M buffer, the cells being recovered each time by centrifugation. All these procedures are carried out at ambient temperature, or preferably slightly lower than ambient, say of about 15° C.

(2) Treatment of the delipidated bacteria by a detergent

The delipidated bacteria so obtained are then subjected to the action of a detergent, preferably SDS within the same buffer, the SDS concentration in the medium ranging from about 0.4 to about 5%, advantageously 4% for a duration of from about 5 minutes to about 1 hour, preferably half of an hour, at a temperature higher than ambiant, ranging notably from 50° to 100° C., preferably of 100° C.

The mixture is then rapidly cooled, more especially in ice until a temperature slightly lower tha ambient is obtained, say of about 6° C.

The non-dissolved parts are eliminated by centrifugation and the supernatant is collected, which supernatant is precipitated by adding 2.5 to 5 volumes, more especially 4 volumes of absolute alcohol cooled down to $-20°$ C.

The medium is centrifuged and the precipitate is dissolved again in a buffer of a pH close to neutral, preferably in a buffer Tris $10^2$M, pH 7.4; the solution is subjected to dialysis against a Tris buffer, say 10 volumes of Tris buffer, for 24 hours, so as to extract, among others, the remaining traces of phenol. The components of the solution (hereafter referred to as "dialysate") which are not entrained through the dialysis membrane, constitute the "crude extract" which may be directly treated by an enzyme, for instance lipase or still preferably DNase, capable of separating the "biologically active fraction" devoid of toxicity, contained in said "crude extract".

(3) Deproteinization of the "crude extract"

Preferably, deproteinization of said hydrosoluble "crude extract" is previously carried out, particularly upon proceeding as follows:

A tris buffered solution phenol mixture containing, say 90% of phenol is added, after its pH has been adjusted to a value close to almost neutral, preferably 7.4, to the above dialysate in an amount such as to finally obtain a mixture of from 40 to 60%, preferably of about 50% in volume of the Tris buffer phenol mixture and of from 60 to 40%, preferably of about 50% in volume of the dialysate.

An incubation of the medium is carried out at a temperature ranging from 60° to 70° C., say of about 68° C., for a duration of from 5 to 30 minutes, preferably of about 10 minutes.

The aqueous phase is recovered after settling and the phenolic phase is washed twice with the same volume of an almost neutral buffer, preferably Tris $10^{-2}$M, pH 7.4.

The aqueous phases are then pooled and subjected to dialysis for a duration of from 24 to 48 hours, against an important volume, say 10 volumes, of distilled water for 1 volume of the aqueous phase to be purified.

The dialysate is then subjected to ultrafiltration or diafiltration on an ultrafiltration membrane which, for instance, admits only molecules having a molecular weight inferior to 10,000 through, so as to eliminte the remaining traces of phenol.

The part remaining on the sieve or "concentrate" is recovered in distilled water and the solution is precipitated by adding from 2.5 to 5 volumes, advantageously 4 volumes of absolute ethanol previously cooled down to −20° C. The precipitation may be improved by the previous addition of a small amount of potassium acetate dosed so as to obtain a salt concentration of about 0.01 M.

The precipitate formed, collected by centrifugation, is dissolved in Tris $10^{-2}$M buffer, having pH close to neutral, preferably 7.4, and the obtained solution is finally lyophilized. The obtained lyophilizate forms the hydrosoluble deproteinized "crude extract" which is then subjected to the action of DNase, lipase or of any other enzyme capable of causing the detachment of the above said "biologically active fraction" substantially free of toxicity, from the components of higher molecular weights contained in said hydrosoluble extract.

(4) Detaching the "biologically active formation" substantially devoid of toxicity When the enzyme consists of a lipase, particularly the Rhizopus lipase, or DNase, it may also be proceeded as follows.

A solution of the above lyophilisate is first formed in a buffer whose pH ranges from 7 to 8, and preferably is 7.6, so as to obtain a "crude extract" concentration of about 1 milligram per milliliter of buffer. The enzyme is then added to the medium in quantities from 25 to 100 micrograms per milliliters, say of 50 micrograms per milliliter. An incubation of the medium is then carried out at a temperature favouring the maximum efficiency of the enzyme, say 37° C., for a duration of, for instance, from 4 to 24 hours.

(5) Separation of the "biologically active fractions"

The incubation mixture is then cooled at ambient temperature and the "biologically active fractions", substantially devoid of toxicity which has become detached from the components of higher molecular weights separated by ultrafiltration or diafiltration, especially through an ultrafiltration membrane, for instance a membrane of the type commercialized under the name "AMICON PM10" which admits only molecules having a molecular weight not exceeding 10,000 to pass therethrough.

The concentrate retained on the membrane may be redissolved in the buffer or diluted with the latter, subjected, if need be, to a second incubation with a new dose of enzyme so as to obtain an additional amount of the "biologically active fraction" prior to proceeding, if necessary, to the lyophilization of the pooled fractions.

Other characteristics of the invention will appear in the course of the non-limitative description of particular extracting procedures of biologically active fractions from gram negative bacteria, and more especially *S.enteritidis* as well as of some of their properties.

The initial bacteria have all been isolated from a strain cultured under conditions described in paragraph A of the following example I. The culturing technique of the bacteria does not belong to the invention and obviously recourse might be had to other cultivation methods such as those described in the literature or likely to be developed by any man skilled in the art.

In the same manner, the process according to the invention might be applied to a starting material consisting of the walls of said bacteria, said walls being obtainable by any process known per se.

EXAMPLE I

A — CULTURE OF *S. ENTERITIDIS*, var. *DANIOZ*, available at INSTITUT PASTEUR, Paris (ATCC 31.194) AND HARVEST OF GRAM NEGATIVE BACTERIA A-1 Culture medium
It contains:
8 g/liter of "Nutrient broth" (Difco)
20 g/liter of the product "Agar-noble" (Difco)

A-2 Utilized material
Roux Flasks

A-3 Preculture in tubes
Tubes of 20×200 containing the medium were seeded starting from a strain cultured on the above medium and pricked out every month (one tube was used for seeding 20 Roux flasks)
tubes were incubated at 37° C. during 24 hours.

A-4 Culture in Roux flasks
each flask contained 200 ml of the medium
160 flasks were seeded in one manufacture batch starting from 8 tubes in which the preculture had been effected over 24 hours
flasks were incubated at 37° C. during 24 hours.

A-5 Harvest procedure
Bacteria were harvested by centrifugation and the residue was taken up in an iced 3% formolized isotonic saline solution so as to obtain a final volume of 2000 ml.

Centrifugation at 3000 g was carried out during 30 minutes.

The residues were taken up in iced isotonic saline solution so as to obtain a final volume of 2000 ml.

washing was carried out during 30 minutes under magnetic stirring;

the foregoing operations were repeated 3 times and the final residue taken up into iced saline isotonic solution, then again washed and centrifuged. 55 g of humid cells corresponding to 5.4 of dry cells were obtained in 160 flasks, that is in 32 liters of the medium.

B — PREPARATION OF A HYDROSOLUBLE "CRUDE EXTRACT" OF *S. ENTERITIDIS*

B - 1 Delipidation of cells 50 g of frozen cells were suspended in a chloroform-/methanol mixture 24/1 (V/V) for obtaining a final volume of 1 liter.

The product so obtained was stirred for one night on a stirring table at a temperature of 20° C.

It was centrifuged at 3000 g for 20 minutes and the supernatant was removed.

The deposit was taken up in 200 ml of Tris $10^{-2}$M of pH 7.6 in order to remove the residual solvents.

This procedure was repeated four times.

After centrifugation at 3000 g for 30 minutes, the delipidated cells were collected.

B - 2 Treatment of the delipidated cells by a detergent

The delipidated cells were taken up in 150 ml of Tris $10^{-2}$M, pH 7.6. 50 ml of a 16% SDS aqueous solution was then added. The final SDS concentration was of 4%.

The mixture was placed for 30 minutes in a boiling water bath, then cooled in crushed ice.

Centrifugation at 10,000 g was carried out for 15 minutes.

The supernatant was collected and dialysed for a night against a Tris $10^{-2}$M solution, pH 7.6.

The volume of the dialysate obtained was 160 ml. 4 volumes of ethylic alcohol, that is 640 ml, were then added to the dialysed solution. A white flaky precipitate was then obtained. The medium was centrifuged at 3000 g for 10 minutes.

The deposit was taken up in 2000 ml of the same buffer.

C — DEPROTEINIZATION OF THE HYDROSOLUBLE "CRUDE EXTRACT"

200 ml of phenol heated at 70° C. and saturated with a Tris $10^{-2}$M buffer, pH 7.6 were added to the preceeding solution.

The mixture was incubated for 10 minutes at 70° C. and then cooled in crushed ice to a temperature of 10° C. Centrifugation was carried out at 3000 g for 30 minutes. An aqueous phase and a phenolic phase were thus obtained.

The phenolic phase was washed four times by 100 ml of the same buffer. The phases were separated, as previously, by centrifugation. The aqueous phases were pooled to form, after diafiltration, 580 ml of aqueous solution. The latter was concentrated to a volume of 60 ml by evaporation under vacuum at a temperature ranging from 37° to 40° C. 6 ml of sodium acetate 0.1 M and 180 ml of absolute ethanol cooled at −20° C. were added thereto.

The obtained medium was left for rest for one night at a temperature of −20° C. and then centrifuged at 10,000 g for 20 minutes. The so obtained precipitate was taken up in 50 ml of Tris $10^{-2}$M, pH 7.4 buffer.

The obtained suspension was dried by lyophilisation. 542 mg of dry product were obtained, which represented a yield of about 10% compared to the weight of the dry cells.

This product had a DO (optically density) of 250 nm of 12 DO/mg. It constituted Fraction C whose biological properties are indicated hereafter.

D — DETACHING THE "BIOLOGICALLY ACTIVE FRACTIONS" SUBSTANTIALLY DEVOID OF TOXICITY

This procedure was carried out on 30 mg of the product obtained at the end of the preceding step. 30 mg of the dry product were suspended in a Tris $10^{-2}$M, pH 7.4 buffer in the proportion of 30 ml for 30 mg.

1.5 mg of Rhizopus lipase were added (Calbiochem. product, specific activity 500 units/mg).

The medium was incubated at 37° C. for 22 hours under magnetic stirring. The reaction was stopped by cooling the mixture in crushed ice.

E - SEPARATION OF THE "BIOLOGICALLY ACTIVE FRACTIONS"

The cooled mixture was subjected to filtration on "AMICON XM100" sieve (product commercialized under said trademark and reference by the AMICON Company).

A filtrate containing 600 μg of product per ml was obtained. This filtrate was filtrated again through an "AMICON PM 10" membrane. A filtrate containing 300 μg of product was obtained.

This product formed the "Fraction D (lipase)" having the following properties:

Its UV spectrum had a maximum absorption at 267 nm. Molecular weights did not exceed about 10,000.

Under the experimental conditions described later, the fraction proved to be active by protecting all animals at a dosis of 0.2 μg per animal.

The animals were not shocked at the time of injection. Animals injected with a dosis of 10 μg, that is 50 times the active dosis, did not show any sign of toxicity 8 days after injection.

EXAMPLE II

DETACHING A "BIOLOGICALLY ACTIVE FRACTION" WITH A RNase AND DNase ASSOCIATION 10 milligrams of deproteinized hydrosoluble "crude extract" (Fraction C of example I) were dissolved in 11 ml of distilled water, until a solution titrating 110 DO was obtained. 0.1 ml of a solution titrating 5.5 mg/ml of RNAse and 0.1 ml of a solution titrating 5.5 mg/ml DNase were introduced in said solution so as to obtain a final concentration of 50 micrograms per milliliter of each one of these enzymes. Incubation was carried out for one hour at 37° C. The reaction was stopped by addition of a phenol/water mixture in the proportion of 90% phenol. The aqueous phase was collected and washed with ether.

The pooled aqueous solutions were then ultrafiltrated through an "AMICON PM10" membrane, in the same manner as in part E, of example I.

8 ml of ultrafiltrate containing 8.7 DO/ml at 268 nm, thus a total of 69.6 DO of active material were obtained.

EXAMPLE III

Quite similar results were obtained when proceeding as in example II, with the exception that the only enzyme used consisted of DNase, in the proportion of 50 micrograms per milliliter.

The non toxic biologically active fractions obtained in examples Ii and III had properties quite similar to those of the non toxic biologically active fractions obtained in example I. Numerical results are indicated in the table hereafter.

EXAMPLE IV

OBTAINING OF A "BIOLOGICALLY ACTIVE FRACTION" FROM A HYDROSOLUBLE "CRUDE EXTRACT" ORIGINATING FROM THE TREATMENT OF SALMONELLA ENTERITIDIS CELLS WITH THE PHENOL-WATER METHOD

A suspension of bacteria in a Tris $10^{-2}$M, pH 7.6, was formed in the proportion of 5 g of dry cells per liter of solution. An equal volume of a mixture of 90% phenol and 10L% of the Tris $10^{-2}$M, pH 7.6 buffer was added to the suspension and the mixture was incubated at 70° C. for 30 minutes. It was then cooled in crushed ice and the aqueous phase separated both from the non solubilized bacterial residues and from the phenolic phase.

The obtained aqueous phase formed the "LPS W" fraction appearing on table I hereafter.

This fraction was subjected to treatments described in parts B, C, D, of example I and the solution obtained was subjected to ultrafiltration through an "AMICON PM10" membrane, whereby an ultrafiltrate was obtained which consisted of the so-called "LPS W — lipase" referred to hereafter.

EXAMPLE V

OBTAINING OF A "HYDROSOLUBLE CRUDE EXTRACT" BY TREATMENT OF ANOTHER STRAIN OF BACTERIAL CELLS WITH A DETERGENT (YB4 FRACTION)

50 g of cells (*Salmonella enteritidis*, ATCC strain n° 31,194) initially frozen, were treated under conditions similar to those which have been described in paragraphs B. and C of example I.

A product was obtained (hereunder referred to as "YB4 fraction") which, when dissolved in water at the rate of 25 mg of dry product in 50 ml of water led to a maximum ultraviolet absorption at 256 nm. Its contents expressed in DO units, was of 5.68 DO per milliliter.

Starting from said YB4 fraction, it was proceeded as follows:

25 mg of the deproteinized YB4 fraction were dissolved in 50 ml of water. The mixture was separated in two aliquot parts.

One of these parts was incubated with DNase, at the rate of 50 mg per milliter, for 2 hours at 37° C.; the other aliquot part was heated at 100° C. for 1 hour 30 prior to being incubated with DNAse under the same conditions as for the first part.

The treatment was then stopped for both parts by cooling with crusehed ice. The obtained fractions were subjected to ultrafiltration on AMICON PM 10 membranes.

The ultrafiltrate obtined from the deproteinized YB4 fraction, which had previously been subjected to preheaing exhibited a 1.35 DO concentration per milliliter, while the ultrafiltrate obtained from the YB4 fraction which had not been previously preheated had only a final 0.25 DO concentration per ml.

The results show the considerable yield increase which resulted from the preheating of the "hydrosoluble crude extract" before its being subjected to the action of the agent required for detaching therefrom the low molecular weight fractions as compared to the results obtained under similar conditions from a non preheated crude fraction.

The obtained fractions (PM 10 filtrates) have also been tested after postheating at 104° C. for 45 minutes).

The results are shown in Table II. The fractions which had been post-heated were devoid of pyrogenicity.

PHARMACOLOGICAL PROPERTIES OF THE "NON TOXIC BIOLOGICALLY ACTIVE FRACTIONS"

Favourable biological properties of the active fractions obtained in examples I to IV, and more particularly their ability to induce a resistance to bacterial infections, and their lack of toxicity, have been evidenced by pharmacological tests described hereafter. The results obtained are gathered in the tables hereafter.

(1) protecting activity against bacterial infection

This test has been carried out in mice. It consists of intraperitonaleously administering to the animal (at the day J —1) the dosis of the active fraction to be studied, then of intravenously administering on the next day (on J day) a dosis of $1.5 \times 10^6$Klebsiella cells (*Klebsiella pneumoniae* strain, ATCC n° 9997), which was lethal after 24 hours for all controls.

The protecting activity of active fractions according to the invention was determined by the survival of treated animals which had been inoculated with infectious Klebsiella cells, 24 hours later.

The doses of the different fractions which have been studied (in micrograms for the tested fractions of example, I, II, III and IV and in DO for the fraction of example V), on the one hand, and the "number of survivals" observed in the different groups of treated mice are indicated in the tables under the general heading "Activity".

The "number of survivals" observed (number on the left) and the number of mice studied in each group and having a given dose of substance (number on the right) are always indicated together under the general heading "Number of survivals".

In these tables, there also appears, as a comparison reference, the results obtained with the corresponding hydrosoluble "crude extracts" from which the different "biologically active fractions" according to the invention originated.

As concerns the "optical density" units (DO) used for determining the weight of dry material contained the treated or obtained solutions, it will be noted that 11 DO approximately correspond to 1 mg of dry substance.

(2) tolerance study

It was determined by means of various tests.

(a) Observation of animals treated with doses of fractions to be studied in view of determining the activity of these various fractions It concerns the doses indicated in columns "Dose (in $\mu$g)" in the part of the Table under the title "Activity". The behaviour of the animals treated by any of the doses was studied. The injection shock, of endotoxinic type appeared immediately, when induced by injection. It is evidence by a characteristic bristling of the fur of animals and an important hypotonicity. This is a qualitative appreciation which, when made, is marked by a cross sign (+) in the column "Shock to injection ". It indicates that at the corresponding dose of substance or fraction under test, an "injection shock" was noticed. On the contrary, the indication "O" represents the qualitative appreciation of the absence of any "injection shock".

(b) Tolerance in normal mice 8 days after inoculation of the dose to be studied

The behaviour of the animals was observed 8 days after intravenous administration of doses which may be 100 to 1,000 times that of the active doses of the tested fractions. Particularly, attention was given to the appearacne of the characteristic fur bristling, hypotonicity and lethality.

The fractions of example V have been tested even more drastically as concerns tolerance, since they were administered to previously surrenalectomized mice.

The results are gathered in the part of the tables appearing under the rubric "Toxicity". The indicated results show the number of mice of each group (number

TABLE I

| FRACTIONS | ACTIVITY | | | TOXICITY | | |
| --- | --- | --- | --- | --- | --- | --- |
| | Dosis (in μg) | Number of survivals | Injection shock | on normal mice | Actino D (12.5γ) on sensitized mice | |
| | | | | | Dosis (in μg) | Survivals |
| "Fraction C" | 1 | 10/10 | + | 200  3/10 | 1 | 0/10 |
| of example I | 0.1 | 18/18 | + | 100  5/10 | 0.1 | 0/10 |
| | 0.05 | 10/10 | 0 | | 0.05 | 0/20 |
| | 0.01 | 0/10 | 0 | | 0.01 | 4/10 |
| "Fraction (D) lipase" of | | | | | | |
| example I | 1 | 8/8 | 0 | | 100 | 5/5 |
| First ultra- | 0.5 | 7/8 | 0 | | | |
| filtrate | 0.2 | 10/10 | 0 | | 10 | 5/5 |
| | 0.1 | 3/10 | | | | |
| "Fraction (D) DNase + RNase" | 1 | 8/8 | 0 | | | |
| of example II | 0.5 | 6/8 | 0 | | | |
| "Fraction (D) DNase" | 1 | 8/8 | 0 | | | |
| of example III | 0.5 | 8/8 | 0 | | | |
| LPS W | 30 | 7/8 | + | | 0.1 | 0/5 |
| of example IV | 20 | 10/10 | + | | 0.05 | 3/5 |
| | 10 | 9/18 | + | | | |
| "Fraction (LPS W + lipase)" | 0.2 | 10/10 | 0 | | | |

TABLE II

Effects of the preheating step on the yield of active fractions of low molecular weights and on their toxicity respectively.

| FRACTIONS | UV peak maxi | Activity assays | | Toxicity for surrenalectomized mice | |
| --- | --- | --- | --- | --- | --- |
| | | Doses | Survivals on 10 | Doses | Survivals on 3 |
| Controls | | 0.1 ml | 0/10 2/10 | | |
| YB$_4$ fraction (no preheating before the action of the DNase - 0.5 mg/ml; 5.68 DO/ml) | 254 nm | 0.01 DO | 8/10 | 0.001 DO | 1/3 |
| | | 0.05 DO | 9/10 | 0.001 DO | 0/3 |
| | | 0.05 DO | 9/10 | 0.002 DO | 0/3 |
| YB$_4$ fraction which underwent a preheating at 100° C. for 1 h 30 before the action of the DNase. | | 0.01 DO | 10/10 | | |
| | | 0.05 DO | 9/10 | | |
| PM 10 filtrate obtained from the YB$_4$ fraction which was not subjected to prior preheating: Yield 4,4% | 258 nm | 0.05 DO | 7/10 | 0.025 DO | 2/3 |
| PM$_{10}$ filtrate obtained from YB$_4$ fraction which underwent prior preheating: Yield 23% | 258 nm | 0.1 DO | 8/10 | 0.1 DO | 3/3 |

The results obtained with "fraction C" of example I, which appear in table I, show that at doses of 100 to 200 micrograms respectively, normal mice undergo an important lethality.

(c) Tolerance in animals sensitized with actinomycine D

The previous injection of 12.5 micrograms of actinomicyne D to mice resulted in a considerable sensitization of the latter to lipopolysaccharide toxicity. Actinomycine D was administered intraperitonaleously to mice at the rate of 12.5 micrograms per animal (Examples I to IV).

The doses of the different tested fractions including, for purpose of comparison, the initial hydrosoluble extracts of examples I and IV, i.e. of "fraction C" and of "fraction LPS W" were administered intravenously.

on the right) and within each group, the number of mice surviving to the corresponding dose.

As concerns "fraction C" of example I, the study of the results reveals a considerable degree of sensitization induced by actinomycine D. 0.05 microgram of the "C fraction" is lethal at 100% for mice. As concerns "fraction LPS" though 3 mice out of 5 treated with 0.05 micrograms of the latter still survived 24 hours after administration, they were then under considerable endotoxinic shock, shortly preceeding death.

Similar observations are to be made as concerns the YB$_4$ fraction of example V. Surrenalectomized mice did not survive to a dose of 0.001 DO.

Comparison between the results obtained with the hydrosoluble "crude extracts" on the one hand, and the active fractions according to the invention, on the other hand, shows the non toxic character, or at least strong reduction of toxicity, of the active fractions according to the invention. Doses of 100 micrograms of the "lipase (D) fractions" of example I induced no death in the corresponding mice.

In the same way, as far as the PM 10 filtrates of example V are concerned, doses of 0.1 DO do not result in the death of surrenalectomized animals, especially when the PM 10 filtrates have been subjected to the above described pre-heating treatment.

The results considered thus show the considerable degree of detoxification or the lack of toxicity of active fractions which the invention permits. While the active doses of the fractions according to the invention (examples I to IV) are of same magnitude as those of the fractions taken as comparison, their "toxicity" is reduced to a considerable amount, compared to that of the corresponding "crude extracts".

As far as the products of example V are concerned, it appears that a dosis of the "biologically active fraction" according to the invention, yields the same protecting effect as the tenth of the same dose of $YB_4$ fraction. Nevertheless, there remains a considerable benefit for all fractions, and more especially those which underwent the above said post-heating treatment, especially as concerns the therapeutical index.

The active fractions according to the invention form highly valuable active principles of drugs, which, among other features, are useful for stimulating immunological defenses, and more especially for preventing and treating infectious diseases, particularly the ones resisting to antibiotics.

The invention also concerns pharmacological compositions containing said active principle, more especially associated to a pharmaceutically acceptable carrier.

It more especially concerns injectable compositions, in which the active fractions according to the invention are associated to an injectable sterile solution, the so obtained solution being administrable intramuscularly, intravenously, or, if need be, through perfusion.

The parenteral administration is the preferred means of administration of the drug according to the invention. It may nevertheless be administered under other forms, either orally, or rectally or under any form enabling its contacting the mucous membranes, for instance under the form of sprays.

Compositions intended to be orally administered advantageously comprize, in addition to pharmaceutically acceptable excipients, a protection agent which protects them from being too seriously damaged when going through the stomach. All formulae known to this end may be resorted to. Recourse may also be had to coatings or capsules which withstand the gastric medium acidity.

We claim:

1. A method for obtaining a non-toxic, antibacterial product of the gram-negative bacteria enterobacteriaceae which comprises:

enzymatically splitting the water-soluble constituents of the exo- and endocellular components of the cell walls of said gram-negative bacteria in an aqueous solution at a pH in the range of about 5 to 9.5, at a temperature up to about 100° C., which cell constituent has a component of a molecular weight not below about 10,000, has the antibacterial property of the endotoxin LPS, is toxic and is stable to prolonged heating to at least 108° C., with an enzyme capable irreversibly enzymatically removing the components which have a molecular weight in the range from about 500 to about 10,000 from those components having a molecular weight above about 12,000, the enzyme being selected from the group consisting of desoxyribonuclease and lipase, maintaining the pH in the range of about 5 to 9.5 and at a temperature below about 100° C. and at which the enzyme is active, forming a portion which contains the lower molecular weight components from about 500 to 12,000, and separating the product which has a molecular weight in the range of about 500 to 12,000 by filtration through a membrane which retains the product of a molecular weight above about 10,000 and separates the product of a molecular weight from about 500 to 10,000, said product being water-soluble, virtually free of toxicity, being antibacterial, not an antigen, stable when heated at a temperature in the range of about 103–107° C. but unstable upon heating above about 107°.

2. The process of claim 1 wherein the desoxyribonculease is a DNase.

3. The process of claim 1 wherein the bacteria is Salmonellae.

4. The process of claim 3 wherein the bacteria is *Salmonella enteridis*.

5. The process of claim 1 for reducing the pyrogenicity of the product which comprises heating the product at a temperature in the range of about 103° to 107° C.

6. The method of claim 1 which comprises deactivating the enzyme prior to the separating step.

7. A biologically active product which is antibacterial and non-toxic, which product is the water-soluble constituent of a molecular weight in the range of about 500 to about 10,000 and of a UV absorption spectrum maximum at a wavelength of from 254 to 270 nm, the exo- and endocellular constituents of the cell walls of the gram-negative bacteria enterobacteriaceae, which constituents have a molecular weight component of a molecular weight in the range of about 500 to about 10,000 and another above about 10,000, which water-soluble constituents has been enzymatically and irreversibly split and separated from the said component which has a molecular weight above about 10,000 by an enzyme selected from the group consisting of desoxyribonuclease and lipase in an aqueous solution at a temperature not above about 100° C. and at a pH in the range of about 5 to 9.5, and which components has been filtered through a membrane which retained the component of a molecular weight above 12,000 and which product is stable to heating in the range of about 103°–107° C., but not above 107° C.

which product is free of endotoxic shock or lethal effect in intravenous administration to mice at a dosage of 10 micrograms per mouse, which mice have been sensitized intraperitonaleously with 12.5 micrograms of actinomycin D and which product provides antibacterial immunity to 10 mice when administered intraperitonaleously to 10 mice at a dosage up to about 20 micrograms per animal one day prior to being injected with $1.5 \times 10^6$ cells of Klebsiella (Klebsiella pneumoniae, ATCC No. 9997).

8. The product of claim 7 which has a molecular weight ranging from about 1000 to about 10,000.

9. The product of claim 7 wherein the molecular weight ranges from about 2000 to about 10,000.

10. The pharmaceutical composition which is antibacterial and which comprises the product of claim 7 and a pharmaceutically acceptable vehicle.

11. The immunological treatment which comprises administering the composition of claim 7 in an antibacterial effective dosage to a patient.

12. The method of claim 11 wherein the administration is to a patient who has an infectious disease which is resistant to an antibiotic.

* * * * *